United States Patent [19]

Tsutsui et al.

[11] Patent Number: 4,990,640

[45] Date of Patent: Feb. 5, 1991

[54] BENZENE-INSOLUBLE ORGANOALUMINUM OXY-COMPOUNDS AND PROCESS FOR PREPARING SAME

[75] Inventors: Toshiyuki Tsutsui; Mamoru Kioka; Akinori Toyota, all of Kuga, Japan

[73] Assignee: Mitsui Petrochemical Industries, Ltd., Tokyo, Japan

[21] Appl. No.: 407,435

[22] Filed: Sep. 14, 1989

[30] Foreign Application Priority Data

| Sep. 14, 1988 | [JP] | Japan | 63-231205 |
| Sep. 14, 1988 | [JP] | Japan | 63-231206 |
| Sep. 14, 1988 | [JP] | Japan | 63-231207 |
| Dec. 26, 1988 | [JP] | Japan | 63-328730 |
| Mar. 28, 1989 | [JP] | Japan | 1-75608 |
| Mar. 28, 1989 | [JP] | Japan | 1-75610 |

[51] Int. Cl.$^5$ .................................................. C07F 5/06
[52] U.S. Cl. ................................................ 556/181; 556/170
[58] Field of Search ........................ 556/170, 175, 181

[56] References Cited

U.S. PATENT DOCUMENTS

| 3,524,870 | 8/1970 | Matzek et al. | 556/181 X |
| 3,736,342 | 5/1973 | Ichiki et al. | 556/181 X |
| 4,250,104 | 2/1981 | Giannini et al. | 556/181 X |

*Primary Examiner*—Arthur C. Prescott
*Attorney, Agent, or Firm*—Sherman and Shalloway

[57] ABSTRACT

In accordance with the present invention, there are provided benzene-insoluble organoaluminum oxy-compounds having less than 10% in terms of Al atom of Al component dissolving in benzene kept at 60° C. and less than 0.09 of a ($D_{1260}/D_{1220}$) of an absorbance ($D_{1260}$) at 1260 cm$^{-1}$ to an absorbance ($D_{1220}$) at 1220 cm$^{-1}$, both obtained by infrared spectrophotometry, and also processes for preparing said benzene-insoluble organoaluminum oxy-compounds.

10 Claims, 2 Drawing Sheets

BENZENE-INSOLUBLE ORGANOALUMINUM OXY-COMPOUNDS AND PROCESS FOR PREPARING SAME

FIELD OF THE INVENTION

This invention relates to organoaluminum oxy-compounds insoluble in hydrocarbon solvents such as benzene and processes for preparing the same, and more particularly to organoaluminum oxy-compounds which are used as catalyst components of olefin polymerization catalysts and which are insoluble in hydrocarbon solvents such as benzene.

BACKGROUND OF THE INVENTION

Heretofore, titanium catalysts composed of titanium compounds and organoaluminum compounds or vanadium catalysts composed of vanadium compounds and organoaluminum compounds have been known as catalysts for use in preparing α-olefin polymers, for example, ethylene polymers or ethylene/α-olefin copolymers.

Generally speaking, ethylene/α-olefin copolymers obtained by using titanium catalysts involved such problems that they are found to have relatively broad molecular weight distribution and compositional distribution and, moreover, are found to be relatively poor in transparency, surface tackiness and dynamic physical properties. Furthermore, ethylene/α-olefin copolymers obtained by using vanadium catalysts were found to be low in polymerization activity and required to adopt deashing operation, though they were found to be narrower in molecular weight distribution and compositional distribution and, moreover, they were improved fairly in transparency, surface tackiness and dynamic physical properties in comparison with ethylene/α-olefin copolymers obtained by using titanium catalysts. Accordingly, the advent of catalyst systems having been further improved in these properties as mentioned above has been desired.

On the one hand, there have been proposed recently processes for preparing ethylene/α-olefin copolymers using catalysts composed of zirconium compounds and aluminoxane as novel Ziegler-type catalysts.

For instance, Japanese Patent L-O-P Publn. No. 19309/1983 discloses a process for preparing ethylene/α-olefin copolymers by polymerizing ethylene and one or two or more $C_3$–$C_{12}$ α-olefins at a temperature of from −50° C. to 200° C. in the presence of a catalyst composed of a transition metal containing compound represented by the following formula (Cyclopentadienyl)$_2$MeRHal wherein R is cyclopentadienyl, $C_1$–$C_6$ alkyl or halogen, Me is a transition metal and Hal is halogen, and a linear aluminoxane represented by the following formula Al$_2$OR$_4$(Al(R)-O)$_n$ wherein R is methyl or ethyl and n is a number of from 4 to 20, or a cyclic aluminoxane represented by the following formula

wherein R and n are as defined above. This publication cited above teaches that the polymerization of ethylene should be carried out in the presence of a small amount such as up to 10% by weight of somewhat long chain α-olefin or mixture thereof in order to regulate a density of the resulting polyethylene.

Japanese Patent L-O-P Publn. No. 95292/1984 discloses an invention relating processes for preparing linear aluminoxanes represented by the following formula

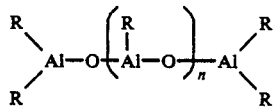

wherein n is 2–40, and R is $C_1$–$C_6$ alkyl, and cyclic aluminoxanes represented by the following formula

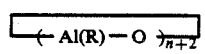

wherein n and R are as defined above. The publication as cited above discloses that at least twenty-five million grams per 1 g of a transition metal and per 1 hour of polyethylene are obtained by carrying out olefin polymerization in the presence of a mixture obtained by the process of said publication, for example, by mixing methylaluminoxane with a bis(cyclopentadienyl) compound of titanium or zirconium.

Japanese Patent L-O-P Publn. No. 35005/1985 discloses a process for preparing polymerization catalysts for olefin which comprises first reacting an aluminoxane compound represented by the following formula

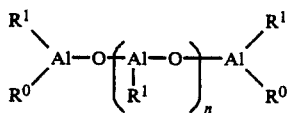

wherein $R^1$ is $C_1$–$C_{10}$ alkyl, and $R^0$ is $R^1$ or represents —O— by linkage, with a magnesium compound, then chlorinating the resulting reaction product, followed by treatment with Ti, V, Zr or Cr compound. This publication as cited above discloses that the above-mentioned catalysts are particularly useful for copolymerization of mixtures of ethylene and $C_3$–$C_{12}$ olefins.

Japanese Patent L-O-P Publn. No. 35006/1985 discloses combinations of mono-, di- or tri-cyclopentadienyl or derivatives thereof and at least two kinds of transition metals (a) and aluminoxane (b) as catalyst systems for use in preparation of reactor blend polymers. Example 1 of the above-cited publication discloses polyethylene having a number average molecular weight of 15,300, a weight average molecular weight of 36,400 and containing 3.4% of propylene component, said polyethylene being obtained by polymerization of ethylene and propylene in the presence of a catalyst composed of bis(pentamethylcyclopentadienyl)zirconium dimethyl and aluminoxane. Further, Example 2 of this publication discloses a blend of polyethylene and ethylene/propylene copolymer having a number average molecular weight of 2,000 and a weight average molecular weight of 8,300 and containing 7.1 mol % of propylene component, which is obtained by polymerization of ethylene and propylene in the presence of a catalyst composed of bis(pentamethylcyclopentadienyl)zirconium dichloride, bis(methylcyclopentadienyl)zirconium dichloride and aluminoxane, said blend comprising a toluene-soluble moiety having a number average molecular weight of 2,200 and a weight average molecular weight of 11,900 and containing 30 mol % of propylene component and a toluene-insoluble moiety having a number average molecular weight of 3,000 and a weight average molecular weight of 7,400 and containing 4.8 mol % of propylene component. Example 3 of this publication further discloses a blend of LLDPE and ethylene/propylene copolymer, which is obtained in the manner similar to that of Example 2 mentioned above, said blend comprising a soluble moiety having a molecular weight distribution ($\overline{M}w/\overline{M}n$) of 4.57 and containing 20.6 mol % of propylene component and an insoluble moiety having a molecular weight distribution of 3.04 and containing 2.9 mol % of propylene component.

Japanese Patent L-O-P Publn. No. 35007/1985 discloses a process for polymerizing ethylene alone or ethylene and α-olefin of at least 3 carbon atoms in the presence of a catalyst system containing metallocene and a cyclic aluminoxane represented by the following formula

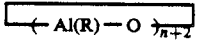

wherein R is alkyl of 1-5 carbon atoms and n is an integer of 1 to about 20, or a linear aluminoxane represented by the following formula

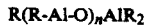

wherein R and n are as defined above. According to the disclosure of the publication cited above, the polymers obtained in the process have weight average molecular weight of about five hundred to about fourteen million and a molecular weight distribution of 1.5–4.0.

Japanese Patent L-O-P Publn. No. 35008/1985 discloses polyethylene or copolymers of ethylene and $C_3$-$C_{10}$ α-olefin having a broad molecular distribution which are prepared by using a catalyst system containing at least two kinds of metallocenes and aluminoxane. The copolymers obtained in this manner are alleged to have a molecular weight distribution ($\overline{M}w/\overline{M}n$) of 2–50.

In Japanese Patent L-O-P Publn. Nos. 260602/1985 and 130604/1985, there are proposed processes for polymerizing olefins in the presence of catalysts formed from mixed organoaluminum compounds comprising aluminoxanes and organoaluminum compounds, and these publications disclose that by virtue of the addition of the organoaluminum compounds, the polymerization activity per unit transition metal improves.

Japanese Patent L-O-P Publn. No. 36390/1987 teaches that aluminoxanes are obtained by reaction of organoaluminum compounds with iron compounds containing water of crystallization, Japanese Patent L-O-P Publn. No. 148491/1987 teaches that aluminoxanes may be obtained by reaction of organoaluminum compounds with compounds containing water of crystallization selected from the group consisting of magnesium compounds, nickel compounds and lanthanide compounds, and Japanese Patent L-O-P Publn. Nos. 56507/1988 and 56508/1988 teach that aluminoxanes can be obtained by reaction of water directly with organoaluminum compounds in inert hydrocarbon solvents utilizing a high speed, high shearing ability induction type impeller or an ultrasonic wave.

In preparing α-olefin (co)polymers in the manner now described, when the aluminoxane compounds are used as one component of the catalyst therefor, α-olefin (co)polymers having a narrow molecular weight distribution and a narrow compositional distribution can be obtained with excellent polymerization activity.

However, a great desideratum for the industry concerned is the advent of such aluminoxane type organoaluminum compounds as having excellent polymerization activity on α-olefin and as being capable of giving olefin (co)polymers having a narrow molecular weight distribution and a narrow compositional distribution.

In this connection, known aluminoxane compounds used hitherto in olefin polymerization, even when they are used in a state of liquid or solid, were prepared and recovered as those which are soluble in hydrocarbon solvents such as benzene or toluene, and their molecular weight was determined by cryoscopic method after dissolving them in benzene and, moreover, a structure of said aluminoxane was decided by measuring a freezing point thereof in benzene.

In light of the foregoing points, the present inventors prosecuted extensive researches and eventually have accomplished the present invention on the basis of their finding that novel organoaluminum oxy-compounds which have not been known at all hitherto and which are insoluble or sparingly soluble in benzene and toluene exhibit excellent catalytic activities in olefin polymerization. The phrase "benzene-insoluble" is used herein to refer to the organoaluminum oxy-compounds of the present invention which are insoluble or only sparingly soluble in benzene and, which are characterized by less than 10% solubility in terms of Al atom in hydrocarbon solvents such as benzene.

OBJECT OF THE INVENTION

The present invention has been accomplished in light of the prior art as mentioned above, and an object of the invention is to provide novel organoaluminum oxy-compounds insoluble in hydrocarbon solvents such as benzene, excellent in catalytic activities and capable of giving olefin (co)polymers having a narrow molecular weight distribution and a narrow compositional distribution, and processes for preparing said novel organoaluminum oxy-compounds.

SUMMARY OF THE INVENTION

The benzene-insoluble organoaluminum oxy-compounds of the present invention are characterized in that:

[A] Al component of said oxy-compound dissolving in benzene kept at 60° C. is less than 10% in terms of Al atom, and

[B] a ratio ($D_{1260}/D_{1220}$) of an absorbance at 1260 $cm^{-1}$ to an absorbance at 1220 $cm^{-1}$, both obtained by infrared spectrophotometry, is less than 0.09.

The first process for preparing benzene-insoluble organoaluminum oxy-compounds of the present invention is characterized by bringing a solution of aluminoxane into contact with water, and Al component soluble in benzene at 60° C. of the resulting benzene-insoluble organoaluminum oxy-compound is less than 10% of Al component in terms of Al atom.

The second process for preparing benzene-insoluble organoaluminum oxy-compounds of the present invention is characterized by bringing a solution of aluminoxane into contact with an active hydrogen containing compound, and Al component soluble in benzene at 60° C. of the resulting benzene-insoluble organoaluminum oxy-compound is less than 10% of Al component in terms of Al atom.

The third process for preparing benzene-insoluble organoaluminum oxy-compounds of the present invention is characterized by bringing an organoaluminum compound into contact with water in such a manner that the amount of organoaluminum atoms dissolved in the reaction system is less than 20% based on the total organoaluminum atoms, and Al component soluble in benzene at 60° C. of the resulting benzene-insoluble organoaluminum oxy-compound is less than 10% of Al component in terms of Al atom.

The benzene-insoluble organoaluminum oxy-compounds obtained in the present invention, when used as one component of catalysts for olefin polymerization, exhibit excellent catalytic activities on olefin polymerization and can give olefin (co)polymers having a narrow molecular weight distribution and a narrow compositional distribution.

DETAILED DESCRIPTION OF THE INVENTION

Hereinafter, the benzene-insoluble organoaluminum oxy-compounds of the present invention and processes for preparing the same are illustrated in detail.

The organoaluminum oxy-compounds of the present invention contain Al component which dissolves in benzene at 60° C. in an amount of less than 10%, preferably less than 5% and further desirably less than 2% in terms of Al atom, and they are insoluble or sparingly soluble in benzene.

Solubility in benzene of such organoaluminum oxy-compounds as mentioned above is obtained by suspending in 100 ml of benzene said organoaluminum oxy-compound in an amount corresponding to 100 mg atoms in terms of Al atom, mixing the resulting suspension at 60° C. for 6 hours, filtering the resulting mixture with G-5 glass filter equipped with a jacket kept at 60° C., and washing four times the solids portion separated on the filter with 50 ml of benzene at 60° C. to measure the amount (x mmol) of Al atoms present in the whole filtrate.

When the benzene-insoluble organoaluminum oxy-compounds of the present invention are analyzed by infrared spectrophotometry (IR), a ratio ($D_{1260}/D_{1220}$) of an absorbance ($D_{1260}$) at around 1260 cm$^{-1}$ to an absorbance ($D_{1220}$) at around 1220 cm$^{-1}$ is less than 0.09, preferably less than 0.08 and particularly in the range of from 0.04 to 0.07.

Infrared spectrophotometric analysis of the organoaluminum oxy-compounds as referred to in the present specification is carried out in the following manner.

First, the organoaluminum oxy-compound is ground, together with nujol, in an agate mortar in a nitrogen box to paste.

Next, the paste-like sample thus obtained is put between KBr plates, and IR spectrum is measured in a nitrogen atmosphere by means of IR-810 manufactured and sold by Nippon Bunko K.K.

Figure 1:
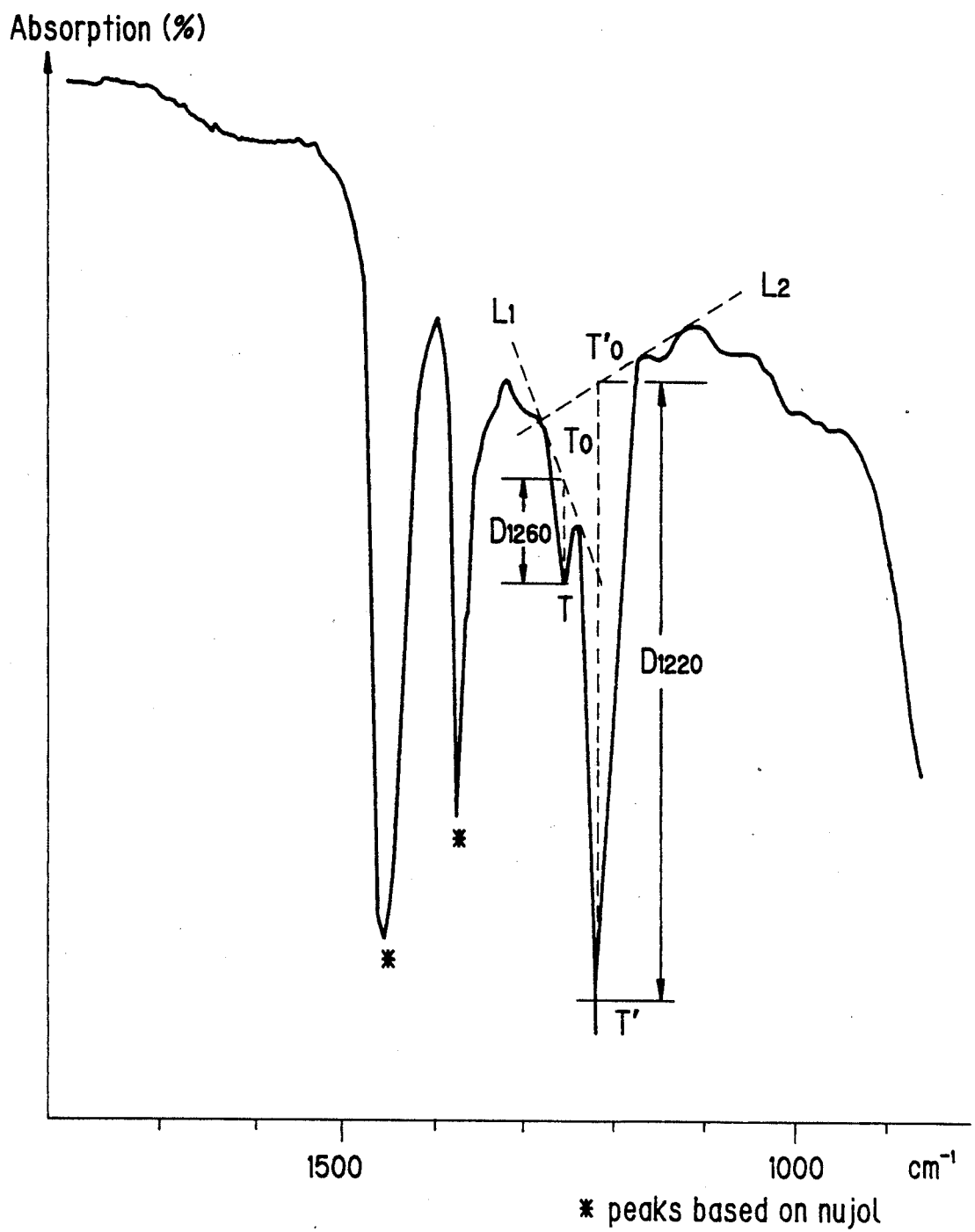
FIG. 1 is a graph showing IR spectrum of the benzene-insoluble organoaluminum oxy-compound of the present invention.

IR spectrum of the organoaluminum oxy-compound of the present invention as obtained is shown in FIG. 1.

From the thus obtained IR spectrum, a $D_{1260}/D_{1220}$ ratio is sought, and a value of said ratio is obtained in the following manner.

(a) A line connecting a maximum point at around 1280 cm$^{-1}$ and a maximum point at around 1240 cm$^{-1}$ is taken as a base line $L_1$.

(b) A transmittance (T %) of an absorption minimum point at around 1260 cm$^{-1}$ and an transmittance ($T_0$%) of a point of intersection are read, said point of intersection being obtained by drawing a vertical line from said absorption minimum point to a wave number abscissa axis (abscissa) and crossing said vertical line with said base line $L_1$, whereby an absorbance ($D_{1260}=\log T_0/T$) is calculated.

(c) Similarly, a line connecting maximum points at around 1280 cm$^{-1}$ and at around 1180 cm$^{-1}$ is taken as a base line $L_2$.

(d) A transmittance (T'%) of an absorption minimum point at around 1220 cm$^{-1}$ and a transmittance ($T'_0$%) of a point of intersection are read, said point of intersection being obtained by drawing a vertical line from said absorption minimum point to a wave number abscissa axis (abscissa) and crossing said vertical line with said base line $L_2$, whereby an absorbance ($D_{1220}=\log T'_0/T'$) is calculated.

(e) From these values as obtained, $D_{1260}/D_{1220}$ is calculated.

Figure 2:
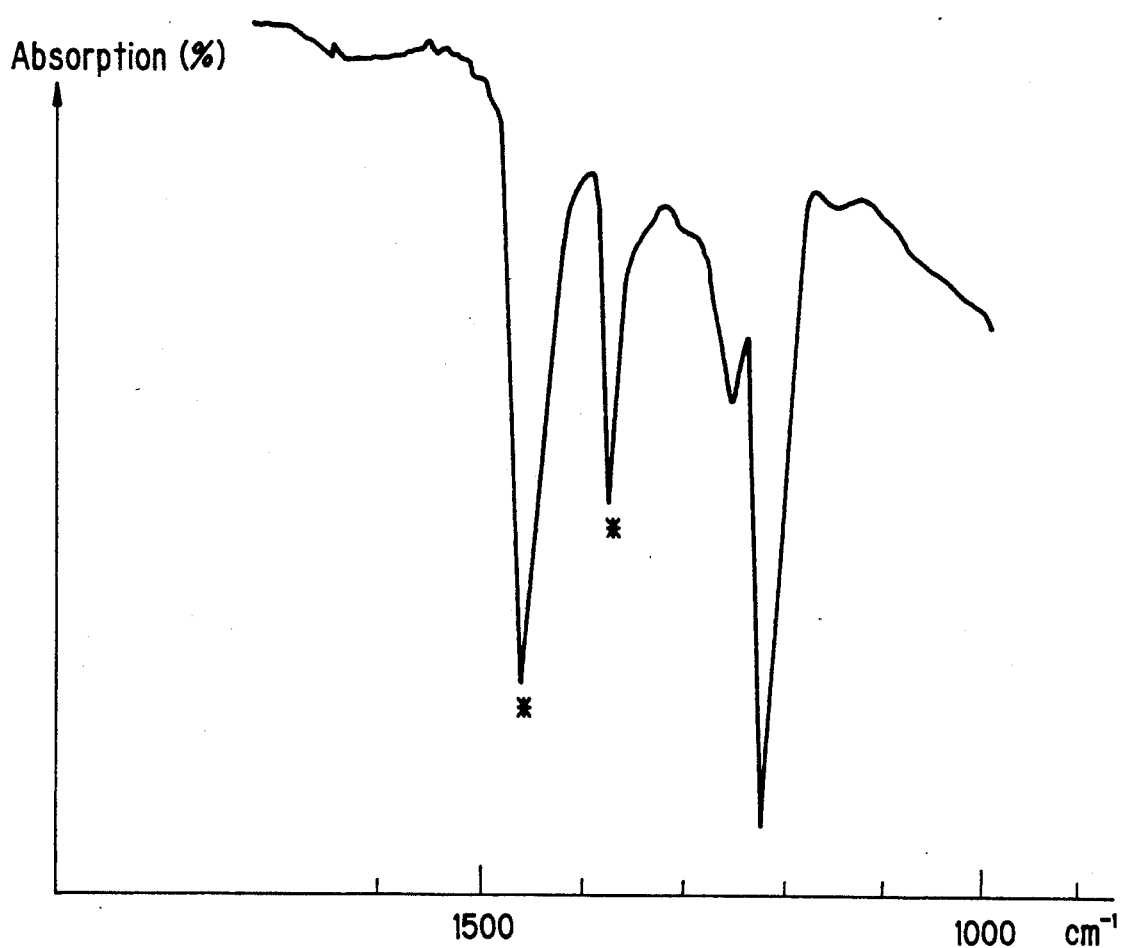
FIG. 2 is a graph showing IR spectrum of a known benzene-soluble organoaluminum compound.

IR spectrum of a known benzene-soluble organoaluminum oxy-compound is shown in FIG. 2. As can be seen from FIG. 2, the benzene-soluble aluminum oxy-compound has a value of $D_{1260}/D_{1220}$ of being virtually 0.10–0.13, and thus the benzene-insoluble organoaluminum oxy-compound of the present invention is apparently different in the value of $D_{1260}/D_{1220}$ from the known benzene-soluble organoaluminum oxy-compound.

The benzene-insoluble organoaluminum oxy-compounds of the present invention are presumed to have an alkyloxyaluminum unit represented by the formula

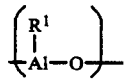

wherein $R^1$ is a hydrocarbon group of 1 to 12 carbon atoms.

In the above-mentioned alkyloxyaluminum unit, $R^1$ includes, for example, methyl, ethyl, n-propyl, isopropyl, n-butyl, isobutyl, pentyl, hexyl, octyl, decyl, cyclohexyl and cyclooctyl. Of these hydrocarbon groups exemplified above, preferred are methyl and ethyl, and particularly preferred is methyl.

In addition to the alkyloxyaluminum unit of the formula

the benzene-insoluble organoaluminum oxy-compounds of the present invention may contain an oxyaluminum unit represented by the formula

wherein $R^1$ is as defined above, and $R^2$ is a hydrocarbon group of 1 to 12 carbon atoms, an alkoxyl group of 1 to 12 carbon atoms, an aryloxy group of 6 to 20 carbon atoms, a hydroxyl group, halogen or hydrogen, provided that $R^1$ and $R^2$ are different from each other. In that case, the organoaluminum oxy-compounds desirably contain the alkyloxyaluminum unit

in a proportion of at least 30 mol %, preferably at least 50 mol % and particularly at least 70 mol %.

The processes for preparing the benzene-insoluble organoaluminum oxy-compounds of the present invention are illustrated below in detail.

The first process for preparing the benzene-insoluble organoaluminum oxy-compounds of the present invention is characterized by bringing a solution of aluminoxane into contact with water.

The second process for preparing the benzene-insoluble organoaluminum oxy-compounds of the present invention is characterized by bringing a solution of aluminoxane into contact with an active hydrogen containing compound.

The solution of aluminoxane used in the present invention may be prepared, for example, by the following procedures.

(1) The procedure for recovering aluminoxanes as their solution in hydrocarbons which comprises reacting organoaluminum compounds such as trialkylaluminum with suspensions in hydrocarbon solvents of compounds having absorbed water or salts containing water of crystallization, for example, hydrates of magnesium chloride, copper sulfate, aluminum sulfate, nickel sulfate or cerous chloride.

(2) The procedure for recovering aluminoxanes as their solution in hydrocarbons which comprises allowing organoaluminum compounds such as trialkylaluminum to interact directly with water, ice or water vapor in solvents such as benzene, toluene, ethyl ether and tetrahydrofuran.

In this connection, the above-mentioned solution of aluminoxane may contain small amount of organometallic components. Furthermore, the solution of aluminoxane recovered by the above-mentioned procedures may be distilled to remove therefrom the solvent or unreacted organoaluminum compound, followed by dissolving again in solvents.

The organoaluminum compounds used for preparing such solutions of aluminoxane as mentioned above include, for example, trialkylaluminum such as trimethylaluminum, triethylaluminum, tripropylaluminum, triisopropylaluminum, tri-n-butylaluminum, triisobutylaluminum, tri-sec-butylaluminum, tri-tert-butylaluminum, tripentylaluminum, trihexylaluminum, trioctylaluminum, tridecylaluminum, tricyclohexylaluminum, tricyclooctylaluminum; dialkylaluminum halides such as dimethylaluminum chloride, diethylaluminum chloride, diethylaluminum bromide and diisobutylaluminum chloride; dialkylaluminum hydrides such as diethylaluminum hydride and diisobutylaluminum hydride; dialkylaluminum alkoxides such as dimethylaluminum methoxide and diethylaluminum ethoxide; and dialkylaluminum aryloxides such as diethylaluminum phenoxide.

Of the organoaluminum compounds as exemplified above, particularly preferred is trialkylaluminum.

Furthermore, there may also be used as the organoaluminum compound isoprenylaluminum represented by the general formula

wherein x, y and z are each a positive number, and $z \geq 2x$.

The organoaluminum compounds mentioned above may be used either singly or in combination.

Solvents used in the solutions of aluminoxane include aromatic hydrocarbons such as benzene, toluene, xylene, cumene and cymeme; aliphatic hydrocarbons such as pentane, hexane, heptane, octane, decane, dodecane, hexadecane and octadecane; alicyclic hydrocarbons such as cyclopentane, cyclohexane, cyclooctane and methylcyclopentane; petroleum fractions such as gasoline, kerosene and gas oil; or halides, particularly chloride and bromides, of the above-mentioned aromatic, aliphatic and alicyclic hydrocarbons. In addition thereto, there may also be used ethers such as ethyl ether and tetrahydrofuran. Of these solvents as exemplified above, particularly preferred are aromatic hydrocarbons.

In the first and second processes for preparing the benzene-insoluble organoaluminum oxy-compounds of the present invention, said benzene-insoluble organoaluminum oxy-compounds are obtained by bringing the above-mentioned solution of aluminoxane into contact with water or active hydrogen containing compounds.

The active hydrogen containing compounds used in the present invention include alcohols such as methanol, ethanol, n-propanol and isopropanol; diols such as ethylene glycol and hydroquinone; and organic acids such as acetic acid and propionic acid. Of these compounds, preferred are alcohols and diols, and especially preferred are alcohols.

Water or the active hydrogen containing compounds with which the solution of aluminoxane is brought into contact may be used as solutions or dispersions in hydrocarbon solvents such as benzene, toluene and hexane, ether solvents such as tetrahydrofuran or amine solvents such as triethylamine, or may be used in the form of vapor or solid. The water with which the solution of aluminoxane is brought into contact may be water of crystallization of salts such as magnesium chloride, magnesium sulfate, copper sulfate, nickel sulfate, iron sulfate and cerous chloride, or absorbed water absorbed to inorganic compounds such as silica, alumina and aluminum hydroxide or polymers.

Reaction of the solution of aluminoxane with water or the active hydrogen containing compounds is carried out usually in solvents, for example, hydrocarbon solvents. The solvents used in this case are aromatic hydrocarbons such as benzene, toluene, xylene, cumene and cymene; aliphatic hydrocarbons such as pentane, hexane, heptane, octane, decane, dodecane, hexadecane and octadecane; alicyclic hydrocarbons such as cyclopentane, cyclohexane, cyclooctane and methylcyclohexane; petroleum fractions such as gasoline, kerosene and gas oil; halogenated hydrocarbons such as halides of the above-mentioned aromatic hydrocarbons, aliphatic hydrocarbons and alicyclic hydrocarbons, particularly, chlorides and bromides; and ethers such as ethyl ether and tetrahydrofuran. Of these solvents as exemplified above, particularly preferred are aromatic hydrocarbons.

In the reaction as mentioned above, water or the active hydrogen containing compound is used in an amount of 0.1–5 moles, preferably 0.2–3 moles to 1 mole of Al atoms present in the solution of aluminoxane. A concentration in terms of aluminum atom in the reaction system is desirably $1\times10^{-3}$–5 gram atom/l, preferably $1\times10^{-2}$–3 gram atom/l, and a concentration of water in the reaction system is desirably $2\times10^{-4}$–5 mol/l, preferably $2\times10^{-3}$–3 mol/l.

The solution of aluminoxane may be brought into contact with water or the active hydrogen containing compound, for example, by the following procedures.

(1) The procedure which comprises bringing the solution of aluminoxane into contact with a hydrocarbon solvent containing water or the active hydrogen containing compound.

(2) The procedure which comprises blowing vapor of water or the active hydrogen containing compound into the solution of aluminoxane, thereby bringing the aluminoxane into contact with the vapor.

(3) The procedure which comprises bringing the solution of aluminoxane into contact directly with water, ice or the active hydrogen containing compound.

(4) The procedure which comprises mixing the solution of aluminoxane with a suspension of an absorbed water containing compound or a water of crystallization containing compound in hydrocarbon, or with a suspension of a compound, to which the active hydrogen containing compound has been absorbed, in hydrocarbon, thereby bringing the aluminoxane into contact with the absorbed water or water of crystallization.

The solution of aluminoxane may contain other components so long as they do not exert adverse effects on the reaction of aluminoxane with water or the active hydrogen containing compound.

The above-mentioned reaction of the solution of aluminoxane with water or the active hydrogen containing compound is carried out usually at $-50°$ to $150°$ C., preferably $0°$–$120°$ C. and more desirably at $20°$–$100°$ C. The reaction time employed is usually 0.5–300 hours, preferably 1–150 hours, though said reaction time varies largely depending upon the reaction temperature used.

The third process for preparing the benzene-insoluble organoaluminum oxy-compounds of the present invention is characterized by obtaining the desired benzene-insoluble organoaluminum oxy-compound by direct contact of the above-mentioned organoaluminum compound with water. In this case, the water is used in such an amount that the organoaluminum atoms dissolved in the reaction system become less than 20% based on the total organoaluminum atoms.

The water which is brought into contact with the organoaluminum compound may be used after dissolving or dispersing it in hydrocarbon solvents such as benzene, toluene and hexane, ether solvents such as tetrahydrofuran or amine solvents such as triethylamine, or may be used in the form of water vapor or ice. Furthermore, as the water, there may also be used water of crystallization of salts such as magnesium chloride, magnesium sulfate, aluminum sulfate, copper sulfate, nickel sulfate, iron sulfate and cerous chloride, or absorbed water absorbed to inorganic compounds such as silica, alumina and aluminum hydroxide or polymers.

The reaction of the organoaluminum compound with water is carried out usually in hydrocarbon solvents. In this case, the hydrocarbon solvents used include aromatic hydrocarbons such as benzene, toluene, xylene, cumene and cymene, aliphatic hydrocarbons such as butane, isobutane, hexane, heptane, octane, decane, dodecane, hexadecane and octadecane, alicyclic hydrocarbons such as cyclopentane, cyclohexane, cyclooctane, cyclodecane, cyclododecane and methylcyclohexane, petroleum fractions such as gasoline, kerosene or gas oil, or halides, particularly chlorides and bromides, of the above-mentioned aromatic, aliphatic and alicyclic hydrocarbons. In addition thereto, there may also be used ethers such as ethyl ether and tetrahydrofuran. Of these solvents as exemplified above, particularly preferred are aromatic hydrocarbons.

Desirably, a concentration in terms of aluminum atom of the organoaluminum compound in the reaction system is usually $1\times10^{-3}$–5 gram atom/l, preferably $1\times10^{-2}$–3 gram atom/l, and a concentration of water in the reaction system is usually $1\times10^{-3}$–20 mol/l, preferably $1\times10^{-3}$–10 mol/l, further preferably $1\times10^{-3}$–5 mol/l and $1\times10^{-2}$–3 mol/l in particular. In this case, the aluminum atoms dissolved in the reaction system is desirably less than 20%, preferably less than 10% and further preferably 0–5% based on the total organoaluminum atoms.

The organoaluminum compound may be brought into contact with water, for example, by the following procedures.

(1) The procedure which comprises bringing a hydrocarbon solution of organoaluminum into contact with a hydrocarbon solution containing water.

(2) The procedure which comprises blowing water vapor into a hydrocarbon solution of organoaluminum, thereby bringing the organoaluminum into contact with water.

(3) The procedure which comprises mixing a hydrocarbon solution of organoaluminum with a hydrocarbon suspension of an absorbed water containing compound or a water of crystallization containing compound, thereby bringing the organoaluminum into contact with the absorbed water or water of crystallization.

(4) The procedure which comprises bringing a hydrocarbon solution of organoaluminum into contact with ice.

The above-mentioned hydrocarbon solution of organoaluminum may contain other components so long as they do not exert adverse effects on the reaction of the organoaluminum with water.

The reaction of the organoaluminum compound with water is carried out usually at a temperature of $-100°$–$150°$ C., preferably $-70°$–$100°$ C. and further preferably $-50°$–$80°$ C. The reaction time, though it varies largely depending upon the reaction temperature employed, is usually 1–200 hours, preferably 2–100 hours.

The benzene-insoluble organoaluminum oxy-compounds of the present invention are used as catalyst components of olefin polymerization catalysts.

Such benzene-insoluble organoaluminum oxy-compounds as mentioned above may be used as olefin polymerization catalysts in combination, for example, with transition metal compounds containing ligands having at least one cycloalkadienyl skeleton and preferably further with organoaluminum compounds.

The transition metal compounds containing ligands having cycloalkadienyl skeletons which are used in combination with the benzene-insoluble organoaluminum oxy-compounds of the present invention are represented by the formula $ML_x$ wherein M is a transition metal, L is a ligand coordinating to the transition metal, at least one L is a ligand having a cycloalkadienyl skeleton, when at least two ligands having a cycloalkadienyl skeleton are contained, at least two ligands having a cycloalkadienyl skeleton may be bonded via a lower alkylene group, L other than the ligand having a cycloalkadienyl skeleton is a hydrocarbon group of 1-12 carbon atoms, an alkoxy group, an aryloxy group, halogen or hydrogen, and x is a valence of the transition metal.

In the above-mentioned formula, M which is a transition metal includes zirconium, titanium, hafnium, chromium or vanadium by preference, and particularly preferred are zirconium and hafnium.

The ligands having a cycloalkadienyl skeleton include, for example, cyclopentadienyl alkyl-substituted cyclopentadienyl groups such as methylcyclopentadienyl, ethylcyclopentadienyl, t-butylcyclopentadienyl, dimethylcyclopentadienyl and pentamethylcyclopentadienyl, and an indenyl group, 4,5,6,7-tetrahydroindenyl group and a fluorenyl group.

Two or more ligands having a cycloalkadienyl skeleton as mentioned above may coordinate to the transition metal and, in this case, at least two ligands having a cycloalkadienyl skeleton may be bonded together via a lower alkylene group.

The ligand other than those having a cycloalkadienyl skeleton is a hydrocarbon group of 1-12 carbon atoms, an alkoxy group, an aryloxy group, halogen or hydrogen.

The hydrocarbon group having 1-12 carbon atoms mentioned above includes, for example, alkyl, cycloalkyl, aryl and aralkyl, and the alkyl group includes methyl, ethyl, propyl, isopropyl and butyl.

The cycloalkyl group mentioned above includes, for example, cyclopentyl and cyclohexyl, the aryl group includes, for example, phenyl and tolyl, and the aralkyl group includes, for example, benzyl and neophyl.

The alkoxy group mentioned above includes, for example, methoxy, ethoxy and butoxy, and the aryloxy group includes, for example, phenoxy.

The halogen mentioned above includes, for example, fluorine, chlorine, bromine and iodine.

Listed below are typical representatives of the transition metal compounds having a cycloalkadienyl skeleton, represented by the aforementioned formula $ML_x$ in which M is zirconium.

Bis(cyclopentadienyl)zirconium monochloride monohydride,
Bis(cyclopentadienyl)zirconium monobromide monohydride,
Bis(cyclopentadienyl)methyl zirconium hydride,
Bis(cyclopentadienyl)ethyl zirconium hydride,
Bis(cyclopentadienyl)phenyl zirconium hydride,
Bis(cyclopentadienyl)benzyl zirconium hydride,
Bis(cyclopentadienyl)neopentyl zirconium hydride,
Bis(methylcyclopentadienyl)zirconium monochloride hydride,
Bis(indenyl)zirconium monochloride monohydride,
Bis(cyclopentadienyl)zirconium dichloride,
Bis(cyclopentadienyl)zirconium dibromide,
Bis(cyclopentadienyl)methyl zirconium monochloride,
Bis(cyclopentadienyl)ethyl zirconium monochloride,
Bis(cyclopentadienyl)cyclohexyl zirconium monochloride,
Bis(cyclopentadienyl)phenyl zirconium monochloride,
Bis(cyclopentadienyl)benzyl zirconium monochloride,
Bis(methylcyclopentadienyl)zirconium dichloride,
Bis(n-butylcyclopentadienyl)zirconium dichloride,
Bis(indenyl)zirconium dichloride,
Bis(indenyl)zirconium dibromide,
Bis(cyclopentadienyl)zirconium dimethyl,
Bis(cyclopentadienyl)zirconium diphenyl,
Bis(cyclopentadienyl)zirconium dibenzyl,
Bis(fluorenyl)zirconium dichloride,
Bis(cyclopentadienyl)zirconium methoxychloride,
Bis(cyclopentadienyl)zirconium ethoxychloride,
Bis(methylcyclopentadienyl)zirconium ethoxychloride,
Bis(cyclopentadienyl)zirconium phenoxychloride,
Ethylenebis(indenyl)dimethyl zirconium,
Ethylenebis(indenyl)diethyl zirconium
Ethylenebis(indenyl)diphenyl zirconium,
Ethylenebis(indenyl)methyl zirconium monochloride,
Ethylenebis(indenyl)ethyl zirconium monochloride,
Ethylenebis(indenyl)methyl zirconium monobromide,
Ethylenebis(indenyl)zirconium dichloride,
Ethylenebis(indenyl)zirconium dibromide,
Ethylenebis(4,5,6,7-tetrahydro-1-indenyl)dimethyl zirconium,
Ethylenebis(4,5,6,7-tetrahydro-1-indenyl)methyl zirconium monochloride,
Ethylenebis(4,5,6,7-tetrahydro-1-indenyl)zirconium dichloride,
Ethylenebis(4,5,6,7-tetrahydro-1-indenyl)zirconium dibromide,
Ethylenebis(4-methyl-1-indenyl)zirconium dichloride,
Ethylenebis(5-methyl-1-indenyl)zirconium dichloride,
Ethylenebis(6-methyl-1-indenyl)zirconium dichloride,
Ethylenebis(7-methyl-1-indenyl)zirconium dichloride,
Ethylenebis(5-methoxy-1-indenyl)zironium dichloride,
Ethylenebis(2,3-dimethyl-1-indenyl)zirconium dichloride,
Ethylenebis(4,7-dimethyl-1-indenyl)zirconium dichloride,
Ethylenebis(4,7-dimethoxy-1-indenyl)zirconium dichloride.

In the zirconium compounds as exemplified above, the zirconium metal may be replaced with a metal of titanium, hafnium, chromium or vanadium, and the resulting compounds may also be used as the transition metal compounds in the present invention.

The benzene-insoluble organoaluminum oxy-compounds of the present invention may be used, together with other organoaluminum compounds, as olefin polymerization catalysts components. In this case, the organoaluminum compounds used may be represented, for example, by the formula $R^6{}_n AlX_{3-n}$ wherein $R^6$ is hydrocarbon of 1-12 carbon atoms, X is halogen and n is 1-3.

In the above-mentioned formula, $R^6$ is hydrocarbon of 1-12 carbon atoms, for example, alkyl, cycloalkyl or aryl, including concretely methyl, ethyl, n-propyl, isopropyl, isobutyl, pentyl, hexyl, octyl, decyl, cyclopentyl, cyclohexyl, phenyl, tolyl, etc.

The above-mentioned organoaluminum compounds used in combination with the benzene-insoluble organoaluminum oxy-compounds of the present invention are those as will be exemplified below.

Trialkylaluminum such as trimethylaluminum, triethylaluminum, triisopropylaluminum, triisobutylaluminum, trihexylaluminum, trioctylaluminum, tri-2-ethylhexylaluminum, etc.

Alkenylaluminum such as isoprenylaluminum, etc.

Dialkylaluminum halides such as dimethylaluminum chloride, diethylaluminum chloride, diisopropylaluminum chloride, diisobutylaluminum chloride, dimethylaluminum bromide, etc.

Alkylaluminum sesquihalides such as methylaluminum sesquichloride, ethylaluminum sesquichloride, butylaluminum sesquichloride, ethylaluminum sesquibromide, etc.

Alkylaluminum dihalides such as methylaluminum dichloride, ethylaluminum dichloride, isopropylaluminum dichloride, ethylaluminum dibromide, etc.

Alkylaluminum hydrides such as diethylaluminum hydride, isobutylaluminum hydride, etc.

Furthermore, there may also be used other organoaluminum compounds represented by the formula $R^6{}_nAlY_{3-n}$ wherein $R^6$ is as defined previously, Y is $-OR^7$, $-OSiR^8{}_3$, $-OAlR^9{}_2$, $-NR^{10}{}_2$, $-SiR^{11}{}_3$ or

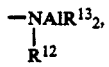

n is 1-2, $R^7$, $R^8$, $R^9$ and $R^{13}$ are each methyl, ethyl, isopropyl, isobutyl, cyclohexyl or phenyl, $R^{10}$ is hydrogen, methyl, ethyl, isopropyl, phenyl or trimethylsilyl, $R^{11}$ and $R^{12}$ are each methyl or ethyl.

The organoaluminum compounds as mentioned above include, in concrete, such compounds as enumerated below.

(i) Compounds of the formula $R^6{}_nAl(OR^7)_{3-n}$ such as dimethylaluminum methoxide, diethylaluminum ethoxide, diisobutylaluminum methoxide, etc.

(ii) Compounds of the formula $R^6{}_nAl(OSiR^8{}_3)_{3-n}$ such as $Et_2Al(OSiMe_3)$, $(iso-Bu)_2Al(OSiMe_3)$, $(iso-Bu)_2Al(OSiEt_3)$, etc.

(iii) Compounds of the formula $R^6{}_nAl(OAlR^9{}_2)_{3-n}$ such as $Et_2AlOAlEt_2$, $(iso-Bu)_2AlOAl(iso-Bu)_2$, etc.

(iv) Compounds of the formula $R^6{}_nAl(NR^{10}{}_2)_{3-n}$ such as $Me_2AlNEt_2$, $Et_2AlNHMe$, $Me_2AlNHEt$, $Et_2AlN(Me_3Si)_2$, $(iso-Bu)_2AlN(Me_3Si)_2$, etc.

(v) Compounds of the formula $R^6{}_nAl(SiR^{11}{}_3)_{3-n}$ such as $(iso-Bu)_2AlSiMe_3$, etc.

(vi) Compounds of the formula

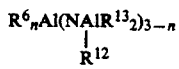

such as

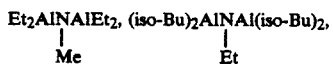

etc.

Of the organoaluminum compounds as exemplified above, preferred are those of the formula $R^6{}_3Al$, $R^6{}_nAl(OR^7)_{3-n}$ and $R^6Al(OAlR^9{}_2)_{3-n}$, particularly those in which $R^6$ is isoalkyl and n=2 are desirable. These organoaluminum compounds may be used in combination of two or more.

The benzene-insoluble organoaluminum oxy-compounds of the present invention are used as olefin polymerization catalysts, preferably in combination with the transition metal compounds containing ligands having such cycloalkadienyl skeleton as mentioned above and further preferably in combination with the above-mentioned organoaluminum compounds. When the organoaluminum compounds are used in combination with the benzene-insoluble organoaluminum oxy-compounds and the transition metal compounds, the resulting catalysts favorably exhibit excellent polymerization activities in polymerization of olefin.

Olefins which can be polymerized by such olefin polymerization catalysts as mentioned above may include ethylene and α-olefins, for example, propylene, 1-butene, 1-pentene, 1-hexene, 4-methyl-1-pentene, 1-octene, 1-decene, 1-dodecene, 1-tetradecene, 1-hexadecene, 1-octadecene, 1-eicocene, cyclopentene, cycloheptene, norbornene, 5-methyl-2-norbornene, tetracyclododecene, 2-methyl-1,4,5,8-dimethano-1,2,3,4,4a,5,8,8a-octahydronaphthalene, etc.

Furthermore, there may be also used styrene, vinylcyclohexane and diene.

In the present invention, polymerization may be carried out by liquid phase polymerization such as solution polymerization and suspension polymerization, or by gas phase polymerization.

Using such olefin polymerization catalysts as mentioned above, olefin is polymerized usually at a temperature of $-50°-200°$ C., preferably $0°-150°$ C. The polymerization is carried out usually at a pressure in the range of from ordinary pressure to 100 kg/cm$^2$, preferably from ordinary pressure to 50 kg/cm$^2$, and the polymerization reaction may be carried out by batch method, semi-continuous method or continuous method. The polymerization may also be carried out, dividing into two or more stages under different reaction conditions. Molecular weight of the resulting olefin polymer may be regulated by hydrogen and/or polymerization temperature.

In practicing polymerization of olefin using such olefin polymerization catalysts as mentioned above, it is desirable to use the benzene-insoluble organoaluminum oxy-compound in an amount of usually $10^{-6}$–0.1 gram atom-Al/l, preferably, $10^{-5}$–$10^{-2}$ gram atom-Al/l, the transition metal compound having a cycloalkadienyl skeleton in an amount of usually $10^{-8}$–$10^{-3}$ mol/l, preferably $10^{-7}$–$10^{-4}$ mol/l, and the organoaluminum compound in an amount of usually 0–0.1 mol/l, preferably $10^{-4}$–$10^{-2}$ mol/l. The ratio of the benzene-insoluble organoaluminum oxy-compound to the organoaluminum compound used in terms of Al atom is desirably 0.01–5, preferably 0.02–2.

Such benzene-insoluble organoaluminum oxy-compounds as mentioned above may also be used after supporting them on solid inorganic compounds such as silica, alumina, magnesium oxide and magnesium chloride, or solid organic compounds such as polyethylene, polypropylene and polystyrene.

Olefin polymerization catalysts composed of the above-mentioned benzene-insoluble organoaluminum oxy-compounds, transition metal compounds having a cycloalkadienyl skeleton and organoaluminum compounds have excellent polymerization activities. That is, the olefin polymerization catalysts of the present invention containing the benzene-insoluble organoaluminum oxy-compounds can give olefin polymers, per unit weight of organoaluminum oxy-compound, about 1.2 to about 20 times the polymers obtained by the use of known olefin polymerization catalysts composed of benzene-soluble aluminoxane and metallocene compounds.

Furthermore, olefin copolymers having a narrow molecular weight distribution and a narrow compositional distribution can be obtained by copolymerizing olefins using the olefin polymerization catalysts containing the benzene-insoluble organoaluminum oxy-compounds of the present invention.

In this connection, the olefin polymerization catalysts of the present invention may contain other useful components for olefin polymerization in addition to the components as mentioned hereinbefore.

EFFECT OF THE INVENTION

The benzene-insoluble organoaluminum oxy-compounds of the present invention exhibit excellent polymerization activities when used as one component of olefin polymerization catalysts, and give olefin copolymers having a narrow molecular weight distribution and a narrow compositional distribution.

The present invention is illustrated below with reference to examples, but it should be construed that the invention is in no way limited to those examples.

REFERENTIAL EXAMPLE 1

Preparation of Aluminoxane

A 400 ml flask thoroughly purged with nitrogen was charged with 37 g of $Al_2(SO_4)_3 \cdot 14H_2O$ and 125 ml of toluene, cooled to 0° C., and 500 mmoles of trimethylaluminum diluted with 125 ml of toluene was added dropwise. The temperature of the flask was elevated to 40° C., and the reaction was continued at that temperature for 10 hours. After the completion of the reaction, the reaction mixture was subjected to solid-liquid separation by filtration, and the toluene was removed from the filtrate, whereby 12 g of white solid aluminoxane was obtained.

EXAMPLE 1

A 400 ml glass flask thoroughly purged with nitrogen was charged with 100 ml of toluene and 3.4 g of $Al_2(SO_4)_3 \cdot 14H_2O$ classified by a 32-mesh screen and left on the screen, and the contents of the flask were brought to a state of suspension. Thereto was added at room temperature 93 ml (2.14 mol-Al/l) of a toluene solution of the aluminoxane prepared in Referential Example 1. Successively, the temperature of the mixture was elevated to 40° C. and stirred at that temperature for 10 days. Thereafter, the mixture thus stirred was classified by an 80-mesh screen in a nitrogen atmosphere to remove the aluminum sulfate compound formed, and a suspension comprising fine particles passed through the screen and toluene was recovered. This suspension was then filtered with G4 glass filter to remove the toluene solution portion, and the solids portion was recovered, followed by suspending it again in toluene. From the results of analysis of sulfate group present in this suspension, it was considered that the amount of aluminum sulfate in said suspension is less than 0.1 mol % in the total aluminum atoms. Separately, a portion of the solids portion recovered above, prior to re-suspending in toluene, was vacuum dried, as it was, at room temperature to obtain a dried solid. This dried solid (organoaluminum oxy-compound) was added in an amount of 100 mmoles in terms of Al atom to a 200 ml reactor equipped with a stirrer, mixed with 100 ml of benzene and stirred at 60° C. for 6 hours. The resulting suspension was filtered through G5 glass filter equipped with a jacket, while maintaining silicone oil poured in the jacket at 60° C., and the filtrate was washed 4 times with 50 ml of benzene kept at 60° C. The resulting filtrate was recovered to measure the amount of Al in the filtrate, whereby Al corresponding to 0.4 mmoles was detected. From this it was considered that the amount of Al component of the above-mentioned solid organoaluminum oxy-compound which dissolves in benzene kept at 60° C. is 0.4% in terms of Al atom.

Further, an infrared spectrum of the above-mentioned solid organoaluminum oxy-compound was measured, whereupon in the IR spectrum measured, an absorption in the Al-O-Al atom group was observed at 600–800 cm$^{-1}$, and the ratio ($D_{1260}/D_{1220}$) of an absorbance ($D_{1260}$) at 1260 cm$^{-1}$ to an absorbance ($D_{1220}$) at 1220 cm$^{-1}$ was 0.068. Evolution of methane was observed when the solid organoaluminum oxy-compound decomposed by water, and said oxy-compound had a specific surface of 30 g/m$^2$.

The benzene-insoluble organoaluminum oxy-compound as prepared above was tested for polymerization activity in the following manner.

A 2 liter stainless steel autoclave thoroughly purged with nitrogen was charged with 900 ml of 4-methyl-1-pentene, followed by rise in temperature up to 50° C. To the autoclave were added 0.22 ml of a suspension of the solid portion obtained in Example 1, i.e. a benzene-insoluble organoaluminum oxy-compound, suspended in toluene (0.44 mole-Al/l) and 1 ml of a solution of (i-Bu)$_2$-Al-O-Al(i-Bu)$_2$ in toluene (1 mole-Al/l). The temperature was further elevated up to 75° C., and then 1 ml of a solution of bis(methylcyclopentadienyl)zirconium dichloride in toluene (0.001 mole-Zr/l) was injected, together with ethylene, into the autoclave to initiate polymerization. The polymerization was carried out at the total pressure of 8 kg/cm$^2$-G and 80° C. for 40 minutes while continuously feeding ethylene, whereby 92.4 g of an ethylene/4-methyl-1-pentene copolymer having MFR of 1.20 g/10 min, a density of 0.888 g/cm$^3$ and $\overline{M}w/\overline{M}n$ of of 2.2.

EXAMPLE 2

A 400 ml glass flask thoroughly purged with nitrogen was charged with 32.8 ml of toluene and 0.78 g of hexahydrate of ground magnesium chloride, and the contents of the flask were slurried. Thereto was added 25 ml of a solution of the aluminoxane prepared in Referential Example 1 in toluene (2.31 moles-Al/l). Thereafter, the resulting slurry was elevated in temperature to 80° C., and stirred at that temperature for 7 hours. Subsequently, the slurry was filtered and separated into a solid and liquid to obtain a benzene-insoluble organoaluminum oxy-compound. A concentration of dissolved aluminum in the filtrate was measured, whereby the concentration was less than the detection limit of 5 mg-Al/l.

Solubility in benzene kept at 60° C. of the solid component as separated above was measured in the same manner as in Example 1, whereby the solubility was 0.3%.

The benzene-insoluble organoaluminum oxy-compound as prepared above was tested for polymerization activity in the following manner.

A 2 liter stainless steel autoclave thoroughly purged with nitrogen was charged with 900 ml of 4-methyl-1-pentene, followed by rise in temperature up to 50° C., and thereto were added 0.22 ml of a suspension of the solid component obtained in Example 2, i.e. a benzene-insoluble organoaluminum oxy-compound, in toluene (0.44 mole-Al/l) and 1 ml of a solution of (i-Bu)$_2$-AlO-Al(i-Bu)$_2$ in toluene (mole-Al/l). After elevating the temperature up to 75° C., 1 ml of a solution of bis(methylcyclopentadienyl)zirconium chloride in toluene (0.001 mole-Zr/l) was injected, together with ethylene, into the autoclave to initiate polymerization. The polymerization was carried out at the total pressure of 8 kg/cm$^2$-G and 80° C. for 40 minutes while continuously feeding ethylene, whereby 95.4 g of an ethylene/4-methyl-1-pentene copolymer having MFR of 1.51 g/10 min, a density of 0.885 g/cm$^3$ and $\overline{M}w/\overline{M}n$ of 2.1 was obtained.

EXAMPLES 3-11

Benzene-insoluble organoaluminum oxy-compounds were prepared in the same operation as in Example 2 under the conditions as described in Table 1. Table 2 shows results of the polymerization activity test on the benzene-insoluble organoaluminum oxy-compounds conducted in the same operation as in Example 2.

EXAMPLE 12

A 400 ml glass flask thoroughly purged with nitrogen was charged with 59.7 ml of toluene, 40.3 ml of a solution of aluminoxane prepared in the same manner as in Referential Example 1 in toluene (Al 2.48 moles-Al/l) and 25 g of Teflon column (2 mm × 1.2 mm) as a dispersing agent. Thereafter, the autoclave was cooled to −5° C., and thereto was added gradually 0.72 ml of water by means of a pipette. Successively, the reaction was carried out at −5° C. for 40 minutes, the temperature was elevated up to 80° C. over a period of 1 hour and the reaction was further continued at that temperature for 3 hours. After this 3-hour reaction, the Teflon column were removed by screening from the reaction mixture which was then filtered into a solid and liquid to obtain a benzene-insoluble organoaluminum oxy-compound. A concentration of dissolved aluminum in the filtrate was measured, whereby the concentration was less than a detection limit of 5 mg-Al/l.

Solubility in benzene kept at 60° C. of the above-mentioned organoaluminum compound as measured in the same manner as in Example 1 was 0.7%. The ratio (D$_{1260}$/D$_{1220}$) of an absorbance (D$_{1260}$) at 1260 cm$^{-1}$ to an absorbance (D$_{1220}$) at 1220 cm$^{-1}$ as measured in the same manner as in Example 1 was 0.053.

A polymerization activity test of the benzene-insoluble organoaluminum oxy-compound prepared above was conducted in the same manner as in Example 2.

The test results obtained are shown in Table 2.

TABLE 2

| Example | Yield of polymer (g) | MFR (g/10 min) | Density (g/cm$^2$) | Mw/Mn |
|---|---|---|---|---|
| 2 | 95.4 | 1.51 | 0.885 | 2.1 |
| 3 | 82.7 | 1.05 | 0.886 | 2.2 |
| 4 | 90.7 | 1.61 | 0.885 | 2.1 |
| 5 | 84.6 | 1.19 | 0.887 | 2.3 |
| 6 | 91.5 | 0.97 | 0.884 | 2.2 |
| 7 | 77.4 | 0.66 | 0.888 | 2.4 |
| 8 | 86.4 | 1.00 | 0.886 | 2.2 |
| 9 | 88.8 | 1.44 | 0.887 | 2.1 |
| 10 | 93.3 | 1.27 | 0.885 | 2.3 |
| 11 | 90.5 | 1.05 | 0.886 | 2.2 |
| 12 | 83.9 | 0.93 | 0.883 | 2.2 |

EXAMPLE 13

A benzene-insoluble organoaluminum oxy-compound was obtained by repeating the same procedure as in Example 1 except that using 170 ml of toluene, 10.2 g of Al$_2$(SO$_4$)$_3$.14H$_2$O and 140 ml of a solution of aluminoxane in toluene (2.14 moles-Al/l) and the reaction was carried out at 80° C. for 6 hours.

Solubility in benzene kept at 60° C. as measured in the same manner as in Example 1 was 0.3%, the D$_{1260}$/D$_{1220}$ ratio obtained by IR measurement was 0.055, and an absorption based on Al-O-Al atom group was observed at 600–800 cm$^{-1}$. Evolution of methane was observed when the compound obtained above is decomposed by water.

A polymerization activity test of the above-mentioned benzene-insoluble organoaluminum oxy-compound was conducted in the same manner as in Example 1, whereby 30.6 g of an ethylene/4-methyl-1-pentene copolymer having MFR of 0.87 g/10 min, a density of 0.885 g/cm$^3$ and $\overline{M}w/\overline{M}n$ of 2.3 was obtained.

COMPARATIVE EXAMPLE 1

The white solid aluminoxane synthesized in Referential Example 1 was added to benzene kept at 60° C., whereby said aluminoxane completely dissolved therein. The D$_{1260}$/D$_{1220}$ ratio as measured by IR was 0.107.

An IR spectrum of the aluminoxane obtained in Referential Example 1 is shown in FIG. 2.

EXAMPLE 14

A 400 ml glass flask thoroughly purged with nitrogen was charged with 60.3 ml of toluene and 89.7 ml of a solution of the aluminoxane prepared in Referential Example 1 in toluene (2.23 moles-Al/l), and the temperature inside the system was kept at 40° C. Thereto was added dropwise 80 mmole of methanol diluted with 50 ml of toluene, and the reaction was carried out at that

TABLE 1

| Ex. | Toluene (ml) | Water of crystallization containing compound (kind) | (g) | Aluminoxane* (ml) | Reaction temp. (°C.) | Reaction time (hr) | Solubility in benzene (%) |
|---|---|---|---|---|---|---|---|
| 2 | 32.8 | MgCl$_2$.6H$_2$O | 0.78 | 25.0 | 80 | 7 | 0.3 |
| 3 | 31.4 | MgCl$_2$.6H$_2$O | 1.11 | 23.9 | 80 | 7 | 0.1 |
| 4 | 32.8 | MgSO$_4$.6.7H$_2$O | 0.83 | 25.0 | 80 | 7 | 0.4 |
| 5 | 32.8 | MgSO$_4$.6.7H$_2$O | 1.25 | 25.0 | 80 | 7 | 0.2 |
| 6 | 35.2 | Al$_2$(SO$_4$)$_3$.14H$_2$O | 1.06 | 26.8 | 80 | 7 | 0.4 |
| 7 | 32.8 | Al$_2$(SO$_4$)$_3$.14H$_2$O | 1.97 | 25.0 | 80 | 7 | 0.1 |
| 8 | 32.8 | Al$_2$(SO$_4$)$_3$.14H$_2$O | 1.48 | 25.0 | 80 | 7 | 0.4 |
| 9 | 32.8 | CuSO$_4$.5H$_2$O | 1.16 | 25.0 | 50 | 20 | 0.3 |
| 10 | 32.8 | NiSO$_4$.6H$_2$O | 1.02 | 25.0 | 60 | 15 | 0.5 |
| 11 | 32.8 | CeCl$_3$.7H$_2$O | 1.23 | 25.0 | 80 | 10 | 0.6 |

*2.31 moles-Al/l temperature for 60 hours. Thereafter, the reaction mixture was subjected to solid-liquid separation by filtration to obtain a solid component, i.e. a benzene-insoluble organoaluminum oxy-compound, (Yield based on Al 67.6%).

A 200 ml reactor equipped with a stirrer was charged with 100 mg atom in terms of Al atom of the benzene-insoluble organoaluminum oxy-compound obtained above and 100 ml of benzene, and the charge was stirred and mixed at 60° C. for 6 hours. The resulting suspension was filtered through G5 glass filter equipped with a jacket while keeping silicone oil poured in the jacket at 60° C., and the filtrate was washed 4 times with 50 ml of benzene kept at 60° C. The filtrate was recovered, and the amount of Al in the filtrate was measured, whereby Al corresponding to 0.4 mmole of Al was detected. That is, it was considered that the amount of Al component of the above-mentioned organoaluminum oxy-compound which dissolves in benzene kept at 60° C. is 0.4% in terms of Al atom. Further, the above-mentioned solid organoaluminum oxy-compound was subjected to IR measurement, whereby an absorption of Al-O-Al atom group was observed at 600–800 cm$^{-1}$ in the IR spectrum as measured. Evolution of methane was observed when the above-mentioned compound was decomposed with water.

A polymerization activity test of the benzene-insoluble organoaluminum compound obtained above was conducted in the following manner.

A 2 liter stainless steel autoclave thoroughly purged with nitrogen was charged with 900 ml of 4-methyl-1-pentene, followed by rise in temperature up to 50° C. To the autoclave were added 0.67 ml of a suspension of the solid portion obtained in Example 1, i.e. a benzene-insoluble organoaluminum oxy-compound, suspended in toluene (0.75 mole-Al/l) and 1 ml of a solution of (i-Bu)$_2$-Al-O-Al(i-Bu)$_2$ in toluene (1 mole-Al/l). The temperature was further elevated up to 75° C., and then 5 ml of a solution of bis(methylcyclopentadienyl)zirconium dichloride in toluene (0.001 mole-Zr/l) was injected, together with ethylene, into the autoclave to initiate polymerization. The polymerization was carried out at the total pressure of 20 kg/cm$^2$-G and 80° C. for 10 minutes while continuously feeding ethylene, whereby 41 g of an ethylene/4-methyl-1-pentene copolymer having an intrinsic viscosity [η] of 3.3 dl/g as measured at 135° C. in decalin.

EXAMPLE 15

A 400 ml glass flask thoroughly purged with nitrogen was charged with 100 ml of toluene and 18.6 g of MgCl$_2$.6H$_2$O classified by a 32-mesh screen and left on the screen, and the contents of the flask were brought to a state of suspension. After cooling the inside of the system to $-5°$ C., 100 ml of trimethylaluminum in toluene (2.5 moles-Al/l) was gradually added dropwise to the system. Successively, the suspension was stirred at 0° to $-5°$ C. for 1 hour, the temperature was elevated to room temperature over a period of 30 minutes, and the stirring was continued at room temperature for 1 hour. The temperature of the suspension was elevated up to 70° C. over a period of 1 hour, and the stirring was continued at that temperature for 96 hours. Thereafter, the reaction mixture was filtered through a 80-mesh screen in a nitrogen atmosphere to remove the magnesium chloride compound therefrom and then subjected to solid-liquid separation by filtration to obtain a benzene-insoluble organoaluminum oxy-compound. A concentration of aluminum dissolved in the filtrate was measured, whereby the concentration was less than the detection limit of 5 mg-Al/l.

Solubility in benzene kept at 60° C. of Al component of the above-mentioned organoaluminum oxy-compound as measured in the same manner as in Example 1 was 0.3% in terms of Al atom. Further, the above-mentioned solid organoaluminum oxy-compound was subjected to IR measurement, whereby an absorption of Al-O-Al atom group was observed in the IR spectrum at 600–800 cm$^{-1}$, and the $D_{1260}/D_{1220}$ ratio as measured was 0.060. Evolution of methane was observed when the oxy-compound was decomposed by water.

A polymerization activity test of the benzene-insoluble organoaluminum oxy-compound as prepared above was conducted in the same manner as in Example 1, whereby 43.1 g of an ethylene/4-methyl-1-pentene copolymer having MFR of 0.38 g/10 min, a density of 0.889 g/cm$^3$ and $\overline{M}w/\overline{M}n$ of 2.3.

EXAMPLE 16

A 400 ml glass flask thoroughly purged with nitrogen was charged with 100 ml of a solution of trimethylaluminum (2.5 moles-Al/l), and the temperature within the system was maintained at 0° C. Thereafter, 50 ml of a suspension of Al$_2$(SO$_4$)$_3$.14H$_2$O in toluene (5 moles-H$_2$O/l) was gradually added dropwise to the flask. Successively, the mixture was stirred at 0° to $-5°$ C. for 30 minutes, then the temperature was elevated to room temperature over a period of 30 minutes, and the stirring was continued at room temperature for 1 hour. The temperature was further elevated up to 40° C. over a period of 30 minutes, and the stirring was continued at that temperature for 24 hours. The temperature of the mixture was cooled again to 0° C., and 25 ml of a suspension of Al$_2$(SO$_4$)$_3$.14H$_2$O in toluene (5 moles-H$_2$O/l) was added to the mixture. The mixture was stirred at 0° to $-5°$ C. for 30 minutes, the temeprature was elevated up to 40° C. over a period of 1 hour, and the stirring was continued at that temperature for 24 hours. The mixture was cooled once more to 0° C., followed by gradual addition dropwise of 25 ml of a suspension of Al$_2$(SO$_4$)$_3$.14H$_2$O in toluene (5 moles-H$_2$O/l). The temperature of the mixture was elevated to 40° C. over a period of 1 hour, and the stirring was effected at that temperature for 72 hours. Thereafter, the reaction mixture was subjected to solid-liquid separation by filtration to obtain a benzene-insoluble organoaluminum oxy-compound. A concentration of aluminum dissolved in the filtrate was measured, whereby the concentration was less than the detection limit of 5 mg-Al/l.

Solubility in benzene kept at 60° C. the thus obtained solid component, i.e. the benzene-insoluble organoaluminum oxy-compound, was measured in the same manner as in Example 1, whereby the solubility was 0.3%.

The polymerization activity test was conducted in the same manner as in Example 1, whereby 45.6 g of an ethylene/4-methyl-1-pentene copolymer having MFR of 0.32 g/10 min, a density of 0.887 g/cm$^3$ and $\overline{M}w/\overline{M}n$ of 2.3 was obtained.

EXAMPLE 17

The samer reactor as used in Example 16 was charged with 100 ml of a suspension of Al$_2$(SO$_4$)$_3$14H$_2$O in toluene (5 moles-H$_2$O/l), and the temperature within the system was maintained at 0° C. Thereafter, 100 ml of a solution of trimethylaluminum in toluene (2.5 moles-Al/l) was gradually added dropwise to the reactor. Successively, the mixture was stirred at 0° to −5° C. for 1 hour, the temperature was elevated up to room temperature over a period of 30 minutes, and the stirring was continued at room temperature for 1.5 hours. The temperature was further elevated up to 40° C., and the stirring was continued at that temperature for 72 hours. Thereafter, the reaction mixture was subjected to solid-liquid separation by filtration to obtain a benzene-insoluble organoaluminum oxy-compound. A concentration of aluminum dissolved in the filtrate was measured, whereby the concentration as measured was less than the detection limit of 5 mg-Al/l.

Solubility in benzene kept at 60° C. of the solid component thus obtained, i.e. the benzene-insoluble organoaluminum oxy-compound, as measured in the same manner as in Example 1 was 0.4%.

The polymerization activity test of the thus obtained organoaluminum oxy-compound was conducted in the same manner as in Example 1, whereby 41.6 g of an ethylene/4-methyl-1-pentene copolymer having $\overline{\text{MFR}}$ of 0.24 g/10 min, a density of 0.890 g/cm$^3$ and $\overline{\text{Mw}}/\overline{\text{Mn}}$ of 2.4 was obtained.

EXAMPLE 18

A 400 ml glass flask thoroughly purged with nitrogen was charged with 49.1 ml of toluene and 0.90 ml of water, and cooled to −60° C. Thereto was added dropwise over a period of 30 minutes 50 ml of a dilute solution of trimethylaluminum in toluene (1.0 mole-Al/l). Subsequently, the temperature was elevated up to −25° C., and the charge was stirred at −20° to −25° C. for 5 hours. Thereafter, the temperature was elevated up to 0° C., and the stirring was continued at a temperature of 0°-5° C. for 1 hour, then at a temperature of 20°-25° C. for 1 hour and further at 80° C. for 2 hours. Thereafter, the reaction mixture was subjected to solid-liquid separation by filtration to obtain a benzene-insoluble organoaluminum oxy-compound. In the filtrate, 5%, based on the charged Al atom, of Al was detected.

Solubility in benzene kept at 60° C. of the benzene-insoluble organoaluminum oxy-compound obtained above was measured to be 1.0%, the $D_{1260}/D_{1220}$ ratio obtained by IR measurement was 0.062, and an absorption of Al-O-Al atom group was observed at 600–800 cm$^{-1}$. Evolution of methane was observed when this organoaluminum oxy-compound is decomposed by water.

The polymerization activity test of the above-mentioned benzene-insoluble organoaluminum oxy-compound was conducted in the same manner as in Example 1, whereby 58.9 g of an ethylene/4-methyl-1-pentane copolymer having $\overline{\text{MFR}}$ of 0.49 g/10 min, a density of 0.889 g/cm$^3$ and $\overline{\text{Mw}}/\overline{\text{Mn}}$ of 2.4 was obtained.

What is claimed is:

1. An organoaluminum oxy-compound insoluble or sparingly soluble in benzene having:
   (A) less than 10% in terms of Al atom of Al component dissolving in benzene kept at 60° C., and
   (B) less than 0.09 of a ($D_{1260}/D_{1220}$) ratio of an absorbance ($D_{1260}$) at 1260 cm$^{-1}$ to an absorbance ($D_{1220}$) at 1220 cm$^{-1}$, both obtained by infrared spectrophotometry.

2. The organoaluminum oxy-compound as claimed in claim 1 wherein the Al component dissolving in benzene kept at 60° C. is less than 2% in terms of Al atom.

3. A process for preparing an organoaluminum oxy-compound insoluble or sparingly soluble in benzene having less that 10% in terms of Al atom of Al component dissolving in benzene kept at 60° C., which comprises bringing a solution of aluminoxane into contact with water.

4. A process for preparing an organoaluminum oxy-compound insoluble or sparingly soluble in benzene having less than 10% in terms of Al atom of Al component dissolving in benzene kept at 60° C., which comprises bringing a solution of aluminoxane into contact with an active hydrogen containing compound.

5. A process for preparing an organoaluminum oxy-compound insoluble or sparingly soluble in benzene having less than 10% in terms of Al atom of Al component dissolving in benzene kept at 60° C., which comprises bringing an organoaluminum compound into contact with water so that the amount of the organoaluminum atoms dissolved in the reaction system is less than 20% based on the total organoaluminum atoms.

6. The process for preparing an organoaluminum oxy-compound as claimed in claim 3, 4 or 5 wherein the Al component dissolving in benzene kept at 60° C. is less than 2% in terms of Al atom.

7. The organoaluminum oxy-compound as claimed in claim 2 having a ($D_{1260}/D_{1220}$) ratio of an absorbance ($D_{1260}$) at 1260 cm$^{-1}$ to an absorbance ($D_{1220}$) at 1220 cm$^{-1}$ of less than 0.08.

8. The organoaluminum oxy-compound as claimed in claim 2 having a ($D_{1260}/D_{1220}$) ratio of an absorbance ($D_{1260}$) at 1260 cm$^{-1}$ to an absorbance ($D_{1260}$) at 1220 cm$^{-1}$ in the range of from 0.04 to 0.07.

9. The process for preparing an organoaluminum oxy-compound insoluble or sparingly soluble in benzene according to claim 4, which comprises bringing a solution of aluminoxane into contact with an alcohol.

10. The process of claim 5 wherein the organoaluminum compound is trialkyl aluminum or isoprenyl aluminum of the formula

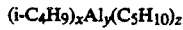

$(i\text{-}C_4H_9)_x Al_y (C_5H_{10})_z$ wherein x, y and z are each a positive number and 2 > 2x.

* * * * *

UNITED STATES PATENT AND TRADEMARK OFFICE
CERTIFICATE OF CORRECTION

PATENT NO.   : 4,990,640
DATED        : February 5, 1991
INVENTOR(S)  : TOSHIYUKI TSUTSUI, ET AL.

It is certified that error appears in the above-identified patent and that said Letters Patent is hereby corrected as shown below:

In the drawings, Sheet 1 and 2, Figures 1 and 2, please change "Absorption (%)" to --Transmittance (%)--.

Signed and Sealed this

Second Day of March, 1993

Attest:

STEPHEN G. KUNIN

Attesting Officer

Acting Commissioner of Patents and Trademarks